(12) United States Patent
Dubowski et al.

(10) Patent No.: US 10,001,480 B2
(45) Date of Patent: Jun. 19, 2018

(54) PHOTO-ELECTROCHEMICAL BIOSENSOR AND SEMICONDUCTOR HETEROSTRUCTURE-BASED SENSING METHOD

(71) Applicant: Jan J. Dubowski, Ottawa (CA)

(72) Inventors: Jan J. Dubowski, Ottawa (CA); Elnaz Nazemi, Gatineau (CA); Srivatsa Aithal, Sherbrooke (CA); Xiaohuan Huang, Wuhan (CN)

( * ) Notice: Subject to any disclaimer, the term of this patent is extended or adjusted under 35 U.S.C. 154(b) by 0 days. days.

(21) Appl. No.: 15/114,660

(22) PCT Filed: Feb. 2, 2015

(86) PCT No.: PCT/CA2015/050073
§ 371 (c)(1),
(2) Date: Jul. 27, 2016

(87) PCT Pub. No.: WO2015/113164
PCT Pub. Date: Aug. 6, 2015

(65) Prior Publication Data
US 2016/0349258 A1    Dec. 1, 2016

Related U.S. Application Data

(60) Provisional application No. 61/934,420, filed on Jan. 31, 2014.

(51) Int. Cl.
*G01N 33/569*        (2006.01)
*G01N 27/327*        (2006.01)
(Continued)

(52) U.S. Cl.
CPC ... *G01N 33/56911* (2013.01); *G01N 27/3275* (2013.01); *G01N 33/48707* (2013.01); *G01N 33/5438* (2013.01); *G01N 33/56983* (2013.01)

(58) Field of Classification Search
CPC ....... G01N 33/56911; G01N 33/48707; G01N 33/5438; G01N 33/56983; G01N 27/3275
(Continued)

(56) References Cited

U.S. PATENT DOCUMENTS 5,081,002 A * 1/1992 Ruberto ............ H01L 21/30612
257/E21.22
5,751,018 A * 5/1998 Alivisatos ......... H01L 21/02422
257/614
(Continued)

OTHER PUBLICATIONS

Matsumoto, H. (1996). "Preparation of Monodisperse CdS Nanocrystals by Size Selective Photocorrosion." J. Phys. Chem. 100: 13781-13785.*
(Continued)

*Primary Examiner* — Jill Alice Warden
*Assistant Examiner* — Jacqueline Brazin
(74) *Attorney, Agent, or Firm* — Benoît & Côté Inc.

(57) ABSTRACT

A photo-electrochemical bio-sensor uses a semiconductor heterostructure located in an etching solution. An outer layer of the heterostructure is functionalized, such as with a self-assembled monolayer, to provide adherence of a charged molecule of interest. When contacted by a test solution, the functionalization immobilizes a quantity of the molecule that corresponds to its concentration in the test solution. The heterostructure undergoes photocorrosion when illuminated by a laser at a rate corresponding to the quantity of immobilized charged molecules. The rate of photocorrosion is monitored to determine the concentration of the molecule in the test solution. The monitoring may make use of a photoluminescent material in the heterostructure that emits photoluminescence in response to the laser illumination. The photoluminescence changes with the advancement of the photocorrosion, and the change is therefore indicative of the concentration of the molecule in the test solution.

27 Claims, 6 Drawing Sheets

Photo-electrochemical sensor

(51) Int. Cl.
*G01N 33/543* (2006.01)
*G01N 33/487* (2006.01)

(58) Field of Classification Search
USPC .......................................... 422/425; 257/64
See application file for complete search history.

(56) References Cited

U.S. PATENT DOCUMENTS

| | | | | |
|---|---|---|---|---|
| 5,990,479 | A * | 11/1999 | Weiss | B82Y 15/00 250/459.1 |
| 8,071,359 | B2 | 12/2011 | Weiss et al. | |
| 8,535,617 | B2 * | 9/2013 | MacDonald | G01N 33/491 422/420 |

OTHER PUBLICATIONS

Matsumoto et al., Preparation of Monodisperse CdS Nanocyrstals by Size Selective Photocorrosion, Journal of Physical Chemistry, vol. 100, No. 32, 1996.

Marshall, Electro-Optic Investigation of the n-Alkanethiol GaAs(OO1): Surface Phenomena and Applications to Photoluminescence-based Biosensing, Doctoral Disertation: University of Sherbrook, Sherbrook, Quebec, Canada, May 2011.

* cited by examiner

PHOTO-ELECTROCHEMICAL BIOSENSOR AND SEMICONDUCTOR HETEROSTRUCTURE-BASED SENSING METHOD

BACKGROUND OF THE INVENTION

Field of the Invention

This invention relates generally to the field of photonic biosensing and, more specifically, to photonic biosensors using semiconductor microstructures.

Description of the Related Art

The need to detect rapidly and with high sensitivity different pathogenic bacteria is highly in demand by the biological research community. Conventional methods of detection of bacteria involving incubation are relatively labour intensive. The culture-based methods take at least twelve hours because they are based on the growth of bacteria to multiply to visible colonies. More rapid detection methods, such as those based on the polymerase chain reaction (PCR) effect, are relatively difficult to automate and they require the presence of highly qualified personnel for both data collection and interpretation. The automated and sensitive detection of bacteria at attractive cost has challenged researchers and is the subject of a continuous investigation that also addresses improved methods of phenotypic assay procedures used in the pharmaceutical field.

SUMMARY OF THE INVENTION

In accordance with the present invention, a photo-electrochemical sensor is provided for detecting the concentration of a charged molecule of interest in a solution under test. The sensor uses a semiconductor heterostructure located in an etching fluid, which may or may not be the solution under test. The heterostructure has an exterior layer that is stable in the absence of a predetermined optical signal, but undergoes photocorrosion by the etching fluid when illuminated by a predetermined optical signal. The exterior layer of the heterostructure is functionalized to provide a specific adherence to the molecule of interest, and the quantity of the charged molecule of interest that is immobilized corresponds to an amount of electrical charge in proximity to the exterior layer. Contact between the exterior layer and the test solution results in immobilization of a quantity of the molecule of interest adjacent to the exterior layer that corresponds to its concentration in the test solution.

With the functionalized semiconductor heterostructure located in the etching fluid, an illumination source, such as a laser, is used to provide a controlled illumination of the heterostructure and induce photocorrosion. The photocorrosion rate is directly influenced by the quantity of the charged molecule that is immobilized on the exterior layer and is therefore indicative of the concentration of the charged molecules in the test solution. The sensor therefore also includes a means for detecting the rate of photocorrosion.

In an exemplary embodiment, the semiconductor has a photoluminescent material that emits photoluminescence in response to the heterostructure being illuminated by the predetermined optical signal. A rate of change of the photoluminescence corresponds to the photocorrosion rate, and a photoluminescence detector is therefore used as the means for detecting the photocorrosion rate. This detector output is therefore also indicative of the concentration of the charged molecules in the test solution.

In one implementation of the invention, the functionalization of the exterior layer of the heterostructure involves a self-assembled monolayer (SAM) deposited on the exterior layer. The SAM provides the specific adherence to the charged molecule of interest and, in one version of the invention, comprises an alkanethiol based material. The SAM may also be treated with ammonium sulfide prior to it being exposed to the test solution.

The semiconductor heterostructure may have a plurality of alternating layers of two different semiconductor materials, and a series of alternating heterointerfaces may be provided that allow multiple uses of the heterostructure by progressive etching of the heterostructure material to sequentially expose the heterointerfaces of interest. One possible form for the semiconductor heterostructure is a GaAs/AlGaAs heterostructure, where the GaAs and AlGaAs are in alternating layers.

The invention has particular application as a biosensor, where the charged molecules being detected are biomolecules. The sensor may therefore be used for detecting a concentration of a particular biomolecule, such as a bacterium or virus, in a solution under test.

DETAILED DESCRIPTION

Figure 1A:
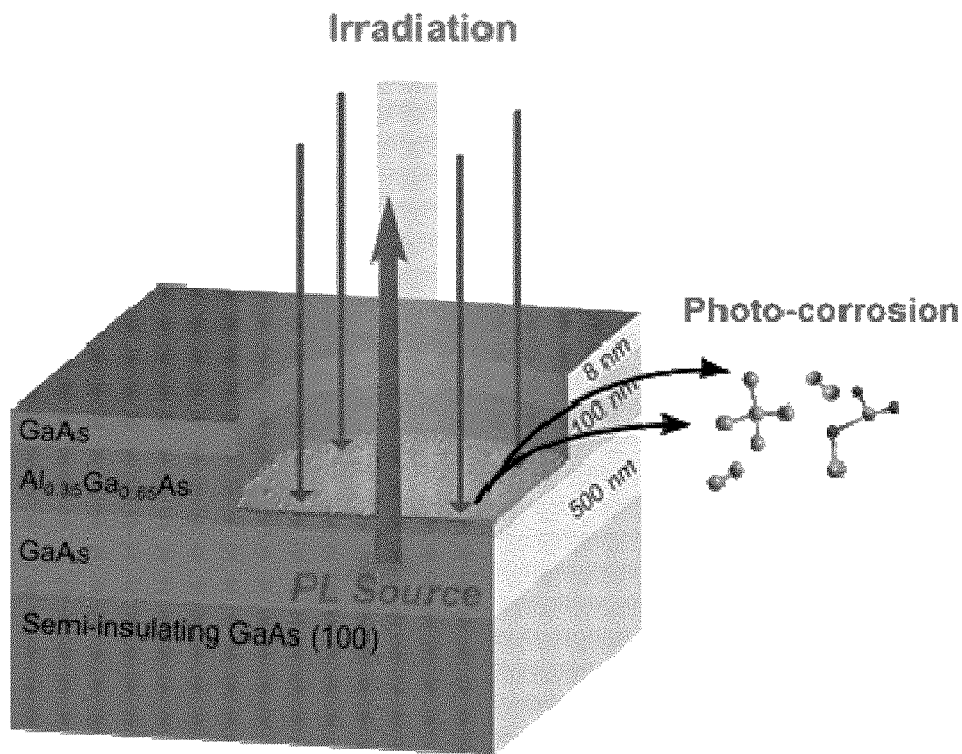
FIG. 1A is a schematic cross-section of a GaAs/AlGaAs heterostructure with a 8 nm thick cap material.

The present invention describes a method and apparatus for monitoring the presence of electrically charged molecules immobilized in the vicinity of a photoluminescence (PL) emitting semiconductor microstructure. The invention takes advantage of microstructures that, if immersed in a soft etching chemical environment, remain optically and structurally stable in the absence of an optical excitation signal. The illumination of these microstructures with photons of energy exceeding the semiconductor bandgap energy, however, not only induces a PL signal, but also induces photo-corrosion of the microstructure exterior.

The invention may make use of any of a variety of different etching fluids, such as deionized water, phosphate buffered saline (PBS) solution, a weak solution of ammonium hydroxide, or solutions with biological molecules (antibodies, bacteria, viruses, etc.), The level of photocorrosion depends on the intensity of the photonic flux and the bending of the semiconductor energy band near the surface, in proportion to the number of holes attracted to the semiconductor surface. For a weakly-doped, or undoped semiconductor, the concentration of corrosion-inducing surface holes, which normally could be controlled by electric biasing of a semiconductor sample, becomes also dependent on the external electric field of charged molecules immobilized in the vicinity of a sample.

The sensitivity of the photocorrosion process to the presence of electrically-charged molecules, immobilized in the vicinity of the surface of an appropriate semiconductor heterostructure, makes it particularly interesting to detection of bacteria, viruses or other biological molecules that are known to carry an electric charge. Photoluminescence (PL) emitting semiconductor quantum well (QW) and quantum dot (QD) microstructures are used in the biosensing fields due to their sensitivity to the presence of surface-trapped molecules that could modify their PL signal. In that context, protection (passivation) of cleaned and etched surfaces of semiconductors from oxidization and adsorption of unwanted molecules plays an important role in biosensor applications. However, to be attractive for biosensing, the passivation process should not affect significantly the ability of an investigated microstructure to detect a low concentration of target molecules. Numerous methods of passivation have been investigated, such as hydrogen plasma treatment, coating the surface with dielectric films of $Si_3N_4$ and coating the surface with organic molecules. Deposition of self-assembled monolayers (SAMs) on the surface of semiconductors forms a basis for immobilization of other molecules. One type of SAM used widely for the passivation of gallium arsenide (GaAs) are n-alkanethiols [$HS(CH_2)_nR$], which are able to make a covalent bond with the surface of GaAs (001) through the formation of S—Ga and S—As bonds. Another approach towards passivation and bio-functionalization of GaAs could involve direct deposition of thiolated oligo-nucleotides or thiolated antibodies.

The process of surface passivation of III-V semiconductors results in enhanced PL emission that is related to the decreased surface recombination velocity (SRV). The effect that surface passivation of GaAs has on SRV reduction has been investigated, e.g., by using organic thiols. An increase in carrier lifetime was observed due to a decrease in trap density or carrier capture cross sections which are two parameters that determine the rate of the SRV. The rate of increase in PL depends on the length of the molecule chain, its hydrophilic characteristics and time of immersion in thiolation solution. The main problem with SAMs is that they are able to cover only 50% of the available sites of cubic semiconductors, such as GaAs (001). This results in a relatively unstable surface of GaAs in a water environment. However, applying some additional surface treatment improves both the passivation and stabilization properties of GaAs. In particular, post-processing of alkanethiol SAMs with ammonium sulfide (AS) may be used to increase photonic stability of GaAs (001). According to X-ray photoelectron spectroscopy (XPS) and Fourier transform IR spectroscopy (FTIR) measurements, this treatment increases the number of sulfur atoms reacting with Ga and As without measurable modification of the quality of the SAMs.

In a first example of the present invention, a GaAs surface is functionalized with SAMs that, following an AS exposure, provide the basis for an antibody-based biosensing architecture suitable for monitoring the biosensor response over a period extending to two hours. Use of the AS processing step slows down the photocorrosion and facilitates recording an effect of photo-electrochemical dissolution of a GaAs/AlGaAs interface modified by the electric charge of bacteria immobilized on the surface of a biosensing device. Consequently, it is possible to detect $E.\ coli$ at $10^3$ CFU/mL (colony forming units/milliliter), with the potential to improve detection sensitivity even further. The details of this example are provided below.

As shown schematically in FIG. 1A, a nominally undoped $GaAs/Al_xGa_{1-x}As$ (x=0.35) heterostructure used in a first example of the invention comprises a GaAs cap (8 nm thick) placed on top of a AlGaAs/GaAs microstructure. The AlGaAs layer located below the cap is 100 nm thick, and a 500 nm thick epitaxial layer of GaAs located below the AlGaAs is the source of the PL signal excited with a homogenized beam of a 532 nm laser and employed for optical monitoring of the device surface perturbation process. To those knowledgeable in the field, it should be evident that the process of monitoring the device surface perturbation could also be carried out with microstructures comprising stacks of quantum well (QW) or quantum dot (QD) layers designed to emit at an arbitrary wavelength. In such a case, the presence of the 500 nm thick layer would be redundant.

Biotinylated poly(ethylene glycol) (PEG) thiols and hexadecane thiol (HDT) were obtained from Prochimia Surfaces (Gdansk, Poland) and Sigma-Aldrich (Ontario, Canada), respectively. Phosphate buffered saline (PBS) solution (10×, pH 7.4) was purchased from Sigma (Oakville, Canada). Polyclonal biotinylated antibodies against $E.\ coli$ were purchased from ViroStat, Inc (Portland, Me.). Neutravidin was bought from molecular probes (Invitrogen, Burlington, Canada). The solvents used to remove impurities form the surface of the heterostructure (the GaAs cap) are OptiClear (bought from National Diagnostics (Mississauga, Canada)), acetone (bought from ACP (Montreal, Canada)) and isopropanol (2-propanol) (bought from Fisher Scientific (Ottawa, Canada)). Ammonium hydroxide 28% ($NH_4OH$) used for etching the wafers was purchased from Anachemia (Richmond, Canada). The live $E.\ coli$ K12 bacteria were obtained from the Department of Biology of the Université de Sherbrooke (Sherbrooke, Canada). They were grown in Luria Bertani (LB) broth and stored at −26° C.

GaAs samples of 2×2 $mm^2$ were cleaned using OptiClear, acetone and isopropanol in an ultrasonic bath (five minutes for each). After the cleaning step, they were dried using a flow of nitrogen and then etched in the concentrated solution of ammonium hydroxide (28%) for two minutes at room temperature to remove the native oxides. After rinsing them with deoxygenized ethanol, they were incubated for twenty hours at room temperature in a mixture of biotinylated PEG thiol and HDT (1:15) diluted in the deoxygenized ethanol to a final concentration of 2 mM. PEG-based thiols were used because they are known to decrease non-specific binding. After the thiolation step, the samples were rinsed with deoxygenized ethanol to get rid of surplus thiol molecules adsorbed on the surface. Thereafter, the samples with biotin terminated SAMs were exposed to 0.1% AS for fifteen minutes and were then rinsed with deionized water (DI-water). The preparation process continued by incubation of the samples for two hours in phosphate buffered saline (PBS) (1×) solution containing 0.2 mg/mL of neutravidin. This step was followed by exposure of the neutravidin coated sample to biotinylated antibodies against *E. coli* diluted in PBS (1×) to a final concentration of 1 μM. The samples were stored for eighteen hours in antibody solution at 4° C.

Due to the discontinuity of the bulk properties of crystals, such as GaAs/AlGaAs (001), and the presence of a significant density of surface states on the surface of GaAs, the band structure of this material experiences a significant bending at the interface with air, water or other mediums. The associated near-surface electric field plays an important role in the behavior of electric carriers excited in this region. For instance, for an n-type semiconductor, this field will drive holes towards the interface and electrons inside the material. This decreases the chance of radiative recombination of electrons ($e^-$) and holes ($h^+$) and is the principal reason for the observed reduced photoluminescence signal from such a semiconductor.

By compensating some of the surface states, the strength of the near-surface electric field may be reduced, which results in a partially recovered GaAs PL signal. Examples of such a process include enhanced PL observed during thiolation of GaAs samples. The formation of the interfacial dipole layer (IDL) near the GaAs surface is also relevant in the context of the PL emission. It is believed that the electric field of the IDL interacts with that of the depletion layer of GaAs and decreases the number of non-radiative recombinations. This results in a reduction of the carrier surface recombination velocity (SRV) and, consequently, may lead to an increased PL signal. Generally, the appearance of excessive electrons at the surface of n-type GaAs should reduce the strength of the near-surface electric field and lead to the increased PL signal. In the situation where the biofunctionalized surface of GaAs immersed in an electrolytic solution is irradiated with photons of energy exceeding its bandgap energy, one has to consider also a photonic stability of such a device. It has been known that photochemical etching, or photocorrosion, of GaAs occurs via the formation of surface oxides that dissolve into solution due to their thermodynamic instability in the acidic environment. This process is described by the following reaction:

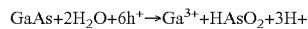

$$GaAs + 2H_2O + 6h^+ \rightarrow Ga^{3+} + HAsO_2 + 3H+$$

The above formula indicates that photocorrosion of GaAs is strongly dependent on the presence of positively charged carriers on the surface of the material. For n-type GaAs, this can be achieved with an illumination source of energy exceeding the semiconductor band gap, typically at an intensity of 1-100 W/cm². Due to the nonlinear character of the efficiency of this process, it has been demonstrated that an illumination of such a material with a 1000-fold weaker intensity light (~10 mW/cm²) could modify the semiconductor surface potential and reduce the photoetching rate by more than 10×. This has applications in localized photochemical etching of multilayered semiconductor materials.

The present invention relies on the ability of an excessive surface electric charge to modify the semiconductor surface potential and reduce or increase the rate of the photocorrosion effect. Normally, layers of such semiconductor heterostructures (such as the GaAs and AlGaAs discussed above) are etched away at a rate determined by the parameters of an excitation source (e.g., a laser) and a reference electrolyte of a relatively weak etching power, such as phosphate buffered saline solution (PBS), water, ammonium hydroxide, etc. Each time a new AlGaAs electrode is presented to the surrounding environment, one can expect to observe a significant change (decrease) in the PL signal intensity, which originates from the 500 nm thick GaAs layer of the structure shown in the example of FIG. 1A. Furthermore, if negatively charged bacteria coated with a layer of positive ions approach the semiconductor electrode, more electrons will be attracted to the surface from the bulk. Thus, the surface potential of the electrode, as well as the concentration of $h^+$ on the electrode surface will be reduced. This will result in a reduced rate of the photocorrosion process, in proportion to the concentration of the negative charge of the bacteria immobilized on, or in the vicinity of, the electrode surface.

Figure 1B:
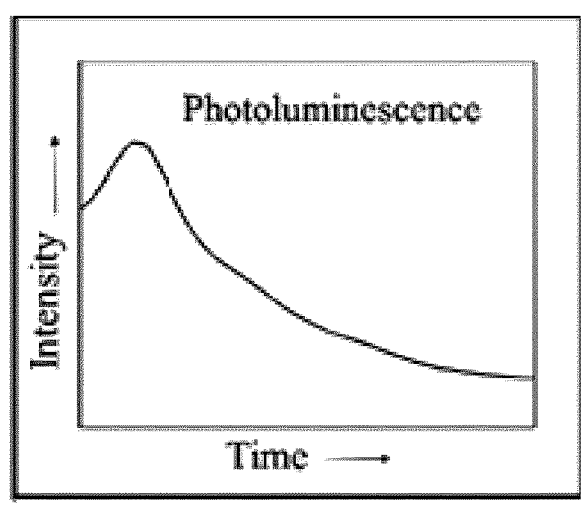
FIG. 1B is a schematic illustration showing the photoluminescence signal measured during photocorrosion of the cap material of the heterostructure of FIG. 1A.

Photocorrosion of the cap GaAs material in the example of FIG. 1A is induced with a spatially homogenized green (532 nm) laser beam that also excites PL from the 500 nm thick GaAs layer. FIG. 1B shows graphically the change in intensity of the 869 nm PL emission with time during the photocorrosion process. The initial increase of the PL signal intensity is related to the chemical dissolution (photocorrosion) of GaAs, induced by holes arriving to the semiconductor surface, and formation of $Ga_2O_3$ on the surface of GaAs exposed to deionized (DI) water or phosphate buffered saline (PBS) solution. This oxide is known to neutralize defects responsible for non-radiative recombination centers and, thus, it passivates electronically the surface of GaAs. As the GaAs cap is etched away, the thickness/density of the $Ga_2O_3$ layer is reduced, which results in formation of a poorly passivated surface and, consequently, reduced PL emission intensity originating from the 500 nm thick GaAs. The time-dependent position of the maximum of the PL signal shown in FIG. 1B depends on a chemical reactivity of the environment surrounding the sample, and on the wavelength and intensity of an irradiation source. For constant irradiation conditions, the greater the concentration of bacteria in the solution the weaker the photocorrosion and, consequently, the more delayed the position of the PL signal maximum.

Figure 1C:
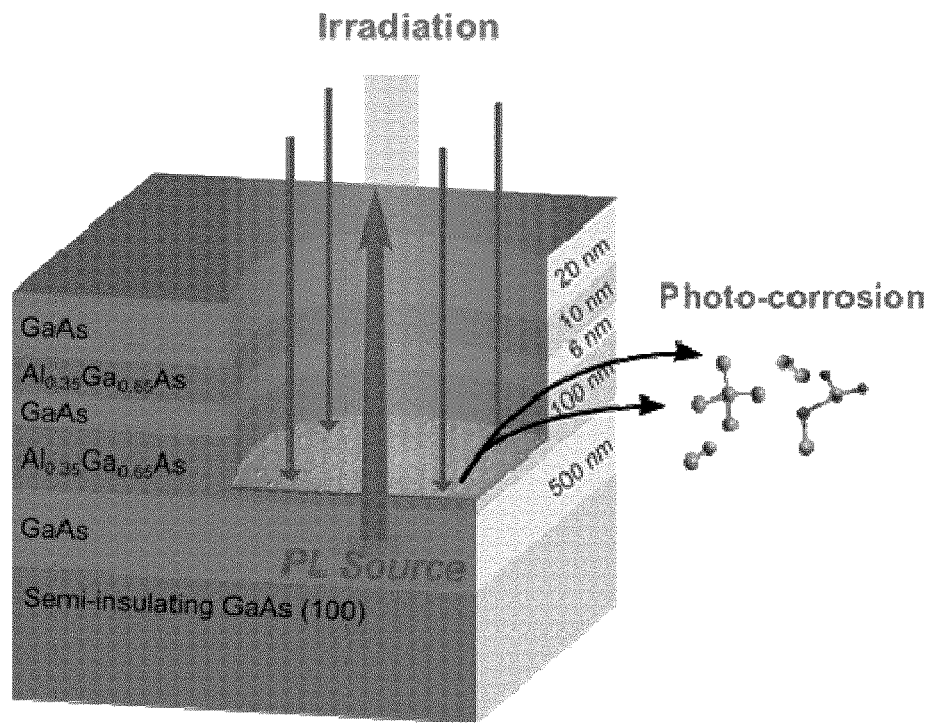
FIG. 1C is a schematic cross-section of a microstructure with a stack of two GaAs/AlGaAs heterojunctions.
Figure 1D:
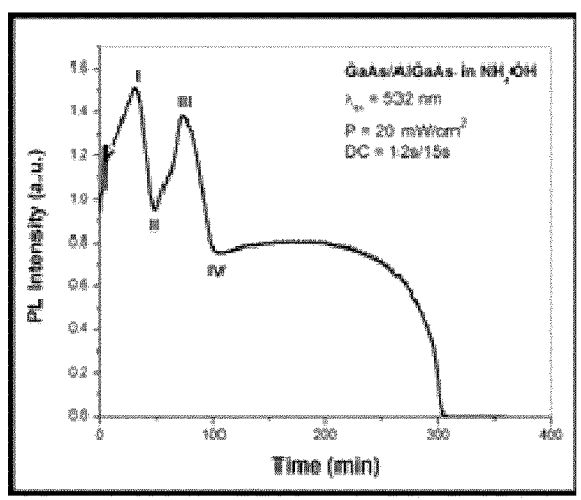
FIG. 1D is a schematic illustration showing the photoluminescence signal measured during photocorrosion of the microstructure of FIG. 1C

Another example semiconductor heterostructure is shown in FIG. 1C. This heterostructure is similar to that of FIG. 1A, but includes a second heterojunction formed by additional layers of GaAs and AlGaAs. Below a 20 nm cap layer of GaAs is a 10 nm layer of Al/Ga/As, followed by a 6 nm layer of GaAs and a 100 nm layer of AlGaAs. As with the FIG. 1A example, a 500 nm GaAs layer below the upper layers provides the photoluminescence signal. The use of two heterojunctions provides two separate locations for carrying out biosensing so that, following etching of the top GaAs/AlGaAs layers, the 6 nm GaAs layer may be biofunctionalized as desired, and the photocorrosion process continued. This allows a second experiment to be conducted using the same heterostructure, with each range of photocorrosion providing separate biosensing data. FIG. 1D shows the overall change in photoluminescence intensity during a sequence of two such experiments. As shown, the first section of the intensity curve, which is similar to the intensity curve of FIG. 1B, rises and falls as expected and then, following refunctionalization, the photocorrosion process recommences, and second portion of the intensity curve shows how the photoluminescence changes during the second biosensing experiment. As discussed below, a semiconductor heterostructure may be constructed to provide many such heterojunctions, thereby allowing it to be used in numerous biosensing experiments.

Figure 1E:
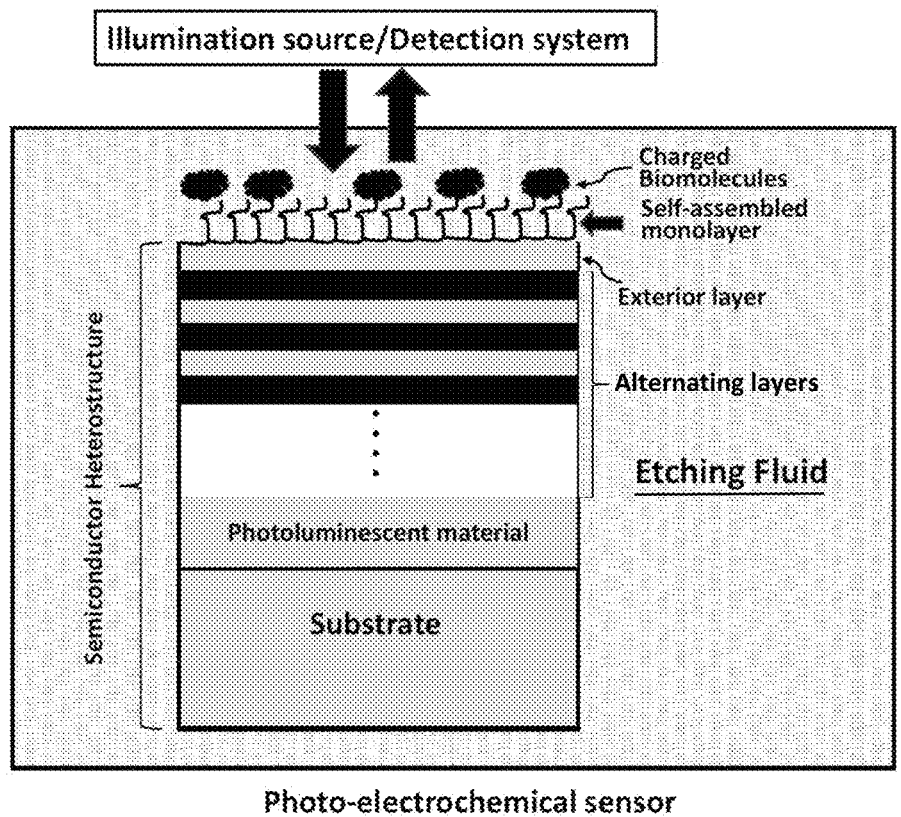
FIG. 1E is a schematic illustration showing a relative arrangement of certain components of a photo-electrochemical sensor according to the invention.

FIG. 1E is a schematic illustration showing a relative arrangement of certain components of a photo-electrochemical sensor according to the invention. The components shown in this figure are common to the embodiments in each of FIGS. 1A and 1C, and are described elsewhere in this disclosure. Other components and layers of the semiconductor heterostructure are omitted from this figure for clarity.

Figure 2:
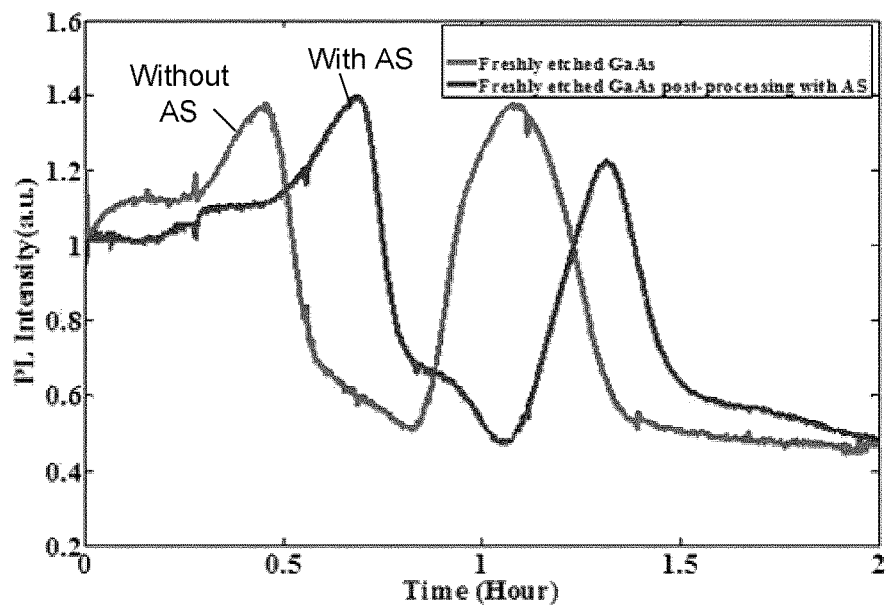
FIG. 2 is a graphical view of in situ PL intensity of freshly etched and AS treated biochips in PBS (duty cycle: 6 s/10 s, laser power: 30 mW/cm$^2$).

Photo-chemical etching of freshly etched and AS treated GaAs/AlGaAs samples immersed in PBS was investigated by recording their PL emission over a period of two hours. The PL of the samples was recorded in situ using a custom designed (Photon etc., Montreal, Canada) Hyperspectral imaging PL mapper (HI-PLM). Two GaAs/AlGaAs biochips were prepared; one of the samples being freshly etched without any biofunctionalization and the other being etched and immersed in an AS solution of 0.1% concentration for fifteen minutes. FIG. 2 shows the time-dependent in situ PL intensity of the two samples.

As the biochips are immersed in PBS and irradiated by a 532 nm laser (~30 mW/cm$^2$) the photo-chemical corrosion process starts. This process is indicated by the presence of two peaks in the PL spectra of the samples. As the 10 nm thick cap layer of GaAs is etched away, the PL signal increases gradually to reach the maximum at 30 and 45 min for the freshly etched GaAs and AS treated samples, respectively. This is followed by the decrease of the PL signal, which corresponds to the situation where the AlGaAs electrodes are gradually exposed to PBS. The appearance of the second PL peak in these plots is related to the presence of the second GaAs layer that is revealed by the photo-etching process. These results illustrate that the photo-etching process of a freshly etched GaAs is significantly faster than that of S-coated GaAs. Given that the XPS results show only a partially S-covered surface, optical attenuation of the PL exciting signal as a possible mechanism behind this effect can be excluded. Rather, the electrons donated by the S atoms appear to be partially responsible for flattening the GaAs band structure near the surface, which results in reduced surface concentration of $h^+$ and, consequently, in a reduced photo-etching effect. As discussed below, an analogous effect of the reduced photo-etching in proportion to the concentration of negatively charged bacteria particles in PBS has also been observed.

Figure 3:
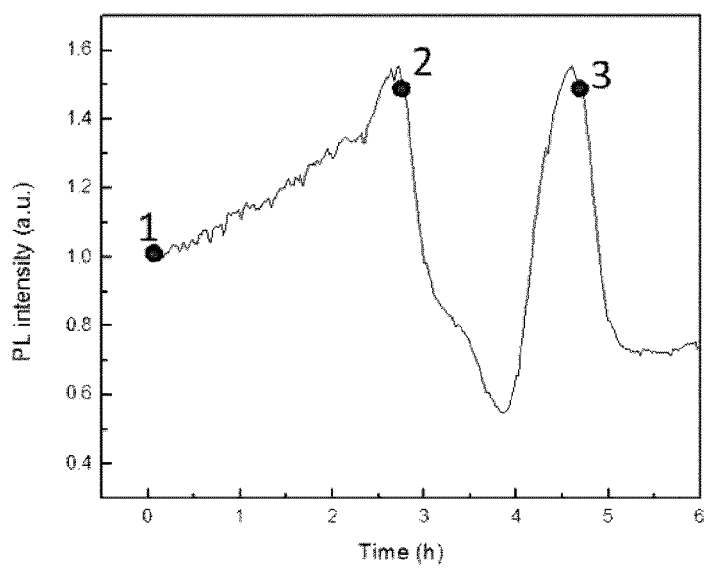
FIG. 3 is a graphical view showing the PL change of freshly etched GaAs in water (duty cycle: 6 s/60 s), and three points indicating the material picked for X-ray photoelectron spectroscopy (XPS) measurements.

The coincidence of the PL intensity peak position with the chemical composition of the investigated heterostructures was verified with XPS measurements. For that purpose, three heterostructures were photo-etched to reach characteristic points on the PL intensity plots as indicated in FIG. 3. Table 1 summarizes the XPS data obtained at these specific points.

TABLE 1

| Atom | Atomic Concentration % (First point) | Atomic Concentration % (Second point) | Atomic Concentration % (Third point) |
|---|---|---|---|
| Ga | 25.72 | 18.13 | 5.13 |
| As | 23.22 | 22.88 | 6.89 |
| Al | 2.83 | 3.88 | 13.98 |

Figure 4A:
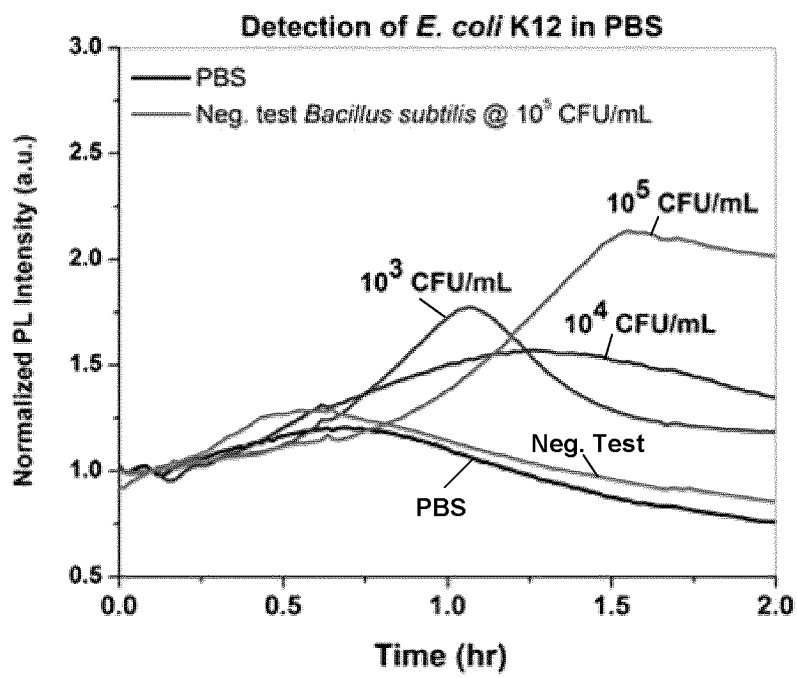
FIG. 4A is a graphical view of the time-dependent PL intensity plots for samples exposed to three concentrations of bacteria diluted in PBS.

Another example of the present invention involves the detection of E. coli in a water solution. After preparation of the GaAs/AlGaAs biochips to the antibody (Ab) level, they were exposed to PBS and different concentrations of E. coli, and their PL emission was recorded in situ over the period of two hours. Following the initial thirty-minute exposure to E. coli solutions, the samples were rinsed with PBS (1×). This time is enough for an antibody-antigen reaction in a liquid/solid interface. The rinsing procedure was used to reduce the contribution to the PL signal from the bacteria non-reacted with Ab. FIG. 4A illustrates the time-dependent PL intensity plots for samples exposed to three concentrations of bacteria diluted in PBS. For comparison, the figure also shows PL plots collected for E. coli Ab biofunctionalized chips exposed to PBS (1×) and Bacilus subtilus (negative test). Negatively charged bacteria in the PBS solution tend to attract positive ions, and upon immobilization in the vicinity of an Ab functionalized GaAs/AlGaAs present as positively charged objects. They will attract electrons from the bulk of the semiconductor and lead to a reduced concentration of holes ($h^+$) that play an important role in the semiconductor dissolution process. These results demonstrate that the PL response of our photo-electrochemical biosensor is very sensitive to the type of the electrolyte (PBS or bacterial solution) surrounding the biochip. More clearly, it can be seen that the position of the PL maximum becomes delayed in proportion to the growing concentration of bacteria in the investigated solutions. At the same time, the results of a negative test confirm the specificity of the antibody selected for detection of E. coli.

Figure 4B:
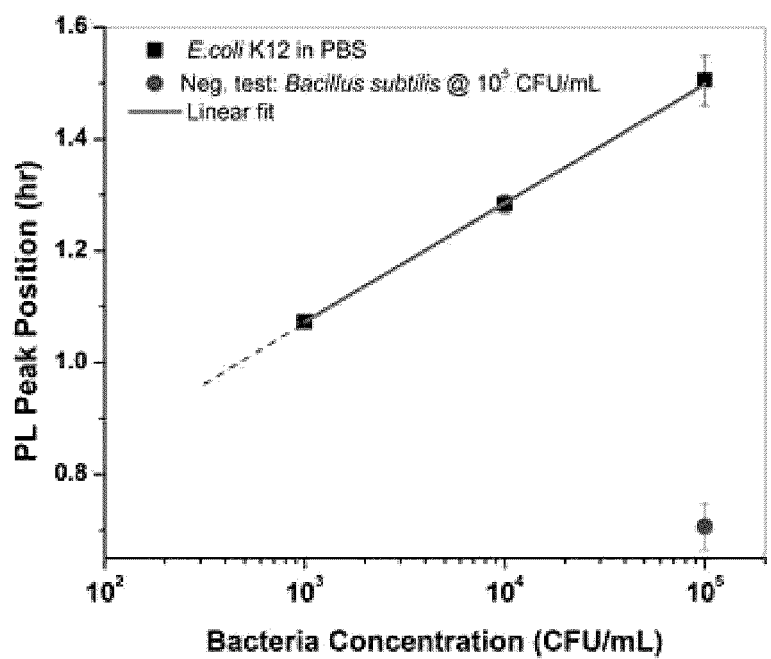
FIG. 4B is a graphical view of a semi-logarithmic plot of the position of PL maxima as a function of the investigated concentrations of bacteria.

The difference in the PL signal intensity observed after a specifically chosen time (e.g., after 1.5 hours in FIG. 4A), or the position of PL signal maxima on the time scale may be used to calibrate the biosensor. FIG. 4B is a graphical view of a semi-logarithmic plot of the position of PL maxima as a function of the investigated concentrations of bacteria. Each point on this plot represents an average of three independent runs. Both specificity and detection at $10^3$ CFU/mL are well illustrated, although it is reasonable to expect that, upon improvement of the experimental conditions, a further improved limit of detection should be achieved.

Figure 5:
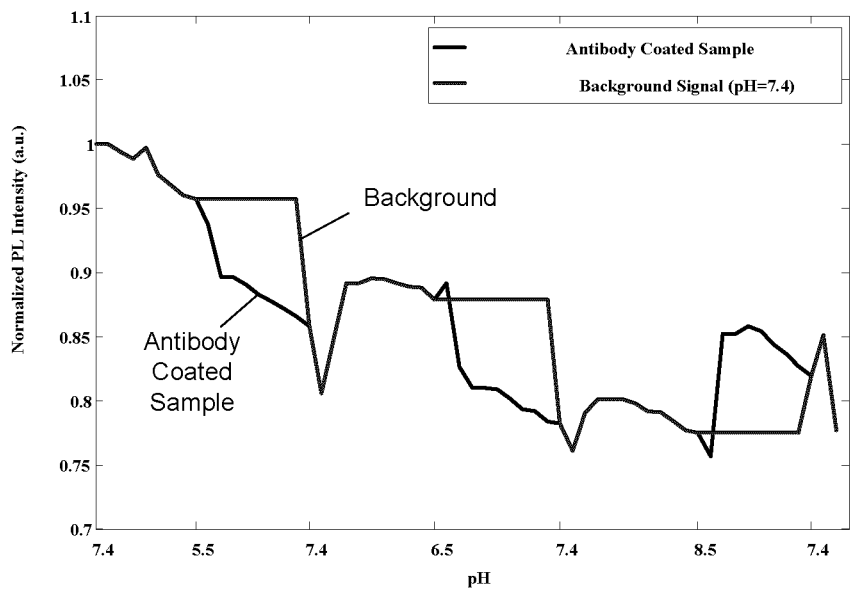
FIG. 5 is a graphical view showing PL variations of E. coli antibody-coated samples exposed to changing pH environments. The background signal is also plotted showing the estimated response of a sample to pH=7.4.
Figure 6:
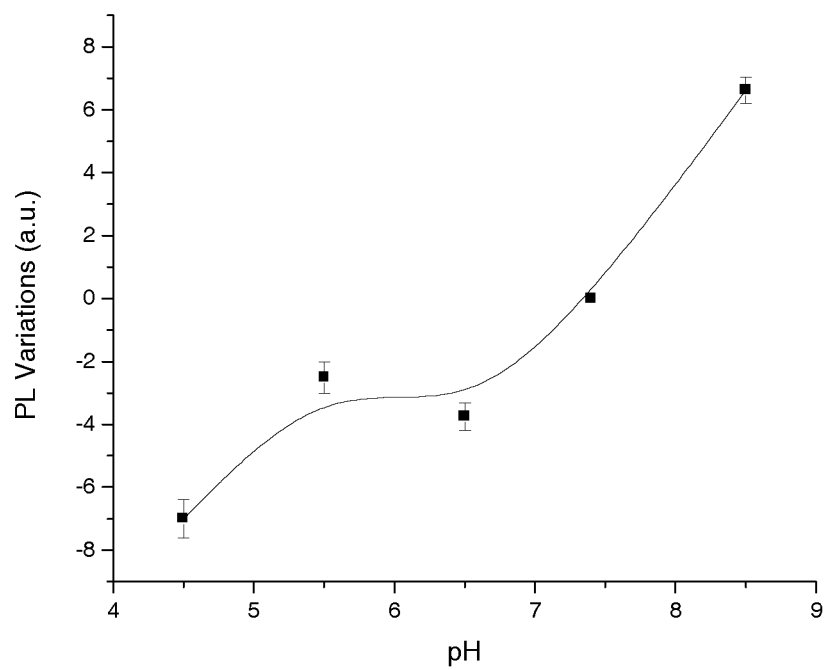
FIG. 6 is a graphical view showing PL variations versus pH for samples functionalized with E. coli antibody.

The pH sensitivity of investigated heterostructures to PBS (1×) of different pH has also been investigated. The heterostructures were functionalized as discussed above. The pH of PBS (1×) was modified by the addition of hydrochloric acid (HCl) and sodium hydroxide (NaOH) to obtain acidic (pH$^-$) and basic (pH$^+$) solutions, respectively. The pH response of antibody-coated samples to changing pH environment is shown in FIG. 5. This figure indicates sensitivity of the biosensor to surface charge. As shown, the PL change follows the pH in each step, increasing with increased pH and decaying with reduced pH. By increasing the pH in each step, the molecules present on the surface of the sample become more negatively charged and contribute to an increase of PL. This effect is in sync with enhancement of PL as the result of immobilization of negatively charged bacteria on the surface of biochips. FIG. 6 shows the dependency of PL variations on the pH of PBS (1×). According to this figure, the biosensor has its highest sensitivity to pH in the ranges of below 5.5 and above 7. It is therefore possible that this effect could allow the detection of bacteria at concentrations lower than $10^3$ CFU/mL.

The instability of semiconductor microstructures in biological fluids has, until now, been considered a parasitical effect (also known, e.g., in photovoltaic applications of semiconductor electrochemical cells). A significant effort has been devoted to passivating, chemically and electronically, semiconductor surfaces of microstructures used for biosensing. However, while the elimination of photocorrosion is considered desirable in conventional approaches, the current innovation makes use of controlled photocorrosion as part of a detection method.

Figure 7:
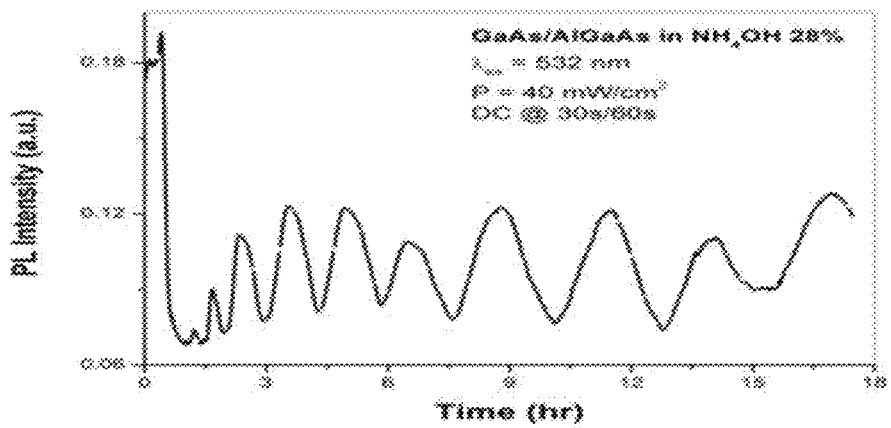
FIG. 7 is a graphical representation of the time-dependent photocorrosion of multiple layers (eleven heterojunctions) of a semiconductor heterostructure according to the present invention.

The photocorrosion effect in the present invention may be used to reveal in situ a series of GaAs surfaces originating from a stack of interfaces such as those in a GaAs/AlGaAs heterostructure. FIG. 7 shows an example of a PL plot collected from a test GaAs/AlGaAs device that undergoes a 532 nm photon-induced photocorrosion in 28% of $NH_4OH$. The PL signal produced originates from a 500 nm thick GaAs layer buried under a stack of MBE-grown GaAs layers separated by 20 nm thick $Al_{0.35}Ga_{0.65}As$ layers. The top GaAs layer has a thickness of 20 nm, and the layers below it start thin and get progressively thicker, beginning at 1 nm and increasing to 2, 4, 6, 8, 10, 20, 30, 40 and finally 50 nm thick. The oscillating PL signal in the figure indicates the photocorrosion of individual heterojunctions located in the investigated stack as well as the thickness of particular layers. The process reveals numerous surfaces suitable for in situ functionalization, while a clearly observed 2nd peak in the plot (at ~70 min) that originates from the dissolution of a 1 nm thick GaAs layer, illustrates a precision of the PL recorded photocorrosion process. A relatively stronger etching environment, in comparison to $H_2O$ or PBS, was employed in this case for the purpose of demonstrating the effect of PL oscillation.

In the above experiment, it was possible to resolve the presence of a 1 nm thick GaAs layer in a photocorroding stack of $GaAs/Al_{0.35}Ga_{0.65}As$ heterostructures. However, it appears that even thinner layers could be observed with this "reverse-MBE (molecular beam epitaxy)" technique, offering a new diagnostic tool, e.g., for the characterization of high-quality epitaxially grown material.

Given the repeatable nature of the photocorrosion effect on a heterostructure having many repeated heterojunctions, an important advantage of the invention is that it allows for sequential in situ biofunctionalization of freshly etched surfaces of the semiconductor and, therefore, multiple biosensing experiments with the same biochip installed in a microfluidic chamber. This should lead to the development of a biosensing device capable of delivering results at a highly attractive cost. For example, following the completion of a 60-90 min long biosensing run, during which photocorrosion of an 8-20 nm thick heterostructure takes place, a new surface of a semiconductor is revealed that is also suitable for biofunctionalization. A new biosensing experiment may therefore be commenced using the same heterostructure. A possible approach would be to use the system for diagnostics requiring one biosensing result per day, providing approximately 20 hours to complete functionalization of the revealed GaAs surface with fresh SAM and antibodies. At least thirty heterojunctions are proposed for microstructures like those shown herein, and it is likely that a large number of events could be monitored with devices comprising stacks of such heterojunctions, quantum wells (QW) or quantum dots (QD).

Quasi-parallel processing is also possible using the present invention. Under pulsed illumination conditions, the time required to produce one point (generated by a pulse of illumination) is, typically, less than two seconds while a typical frequency of data collection is one point per 60-90 seconds. During the off period between two illumination/data collection events, the photocorrosion products diffuse away from the semiconductor-electrolyte interface and, ultimately, become distributed evenly within the etching solution. Thus, there is a significant time window during which the illuminating laser and photoluminescence detection equipment is idle. It is therefore possible to pursue other biosensing experiments in the same time window by presenting a series of other semiconductor microstructures for consecutive illumination/detection. With the ability to do many (e.g., more than 30) experiments during the same time period with the same illumination/detection equipment, it should be possible to design a family of biosensing devices for delivering results at a highly attractive cost.

The invention claimed is:

1. A photo-electrochemical sensor for detecting the concentration of a charged molecule of interest in a solution under test comprising:
   an etching fluid;
   a semiconductor heterostructure located in the etching fluid that has an exterior layer that is stable in the absence of a predetermined optical signal and that undergoes photocorrosion by the etching fluid when illuminated by said optical signal, the exterior layer being functionalized to provide a specific adherence to the charged molecule of interest, such that contact between the exterior layer and the solution under test results in immobilization of a quantity of said charged molecule on the exterior layer that corresponds to its concentration in the test solution;
   an illumination source for providing a controlled illumination of the heterostructure with the predetermined optical signal; and
   a means for detecting a rate of photocorrosion of said exterior layer, said photocorrosion rate being influenced by the immobilized molecules in a manner that is indicative of said quantity of biomolecules immobilized on the exterior layer.

2. A sensor according to claim 1 wherein the exterior layer of the heterostructure is functionalized using a self-assembled monolayer (SAM) deposited on said exterior layer, the SAM providing said specific adherence to the charged molecule of interest.

3. A sensor according to claim 2 wherein the SAM comprises an alkanethiol based material.

4. A sensor according to claim 2 wherein the SAM is treated with a chemical reagent that precipitates sulphur.

5. A sensor according to claim 1, wherein the quantity of said charged molecule of interest that is immobilized corresponds to an amount of electrical charge in proximity to said exterior layer.

6. A sensor according to claim 1 wherein the semiconductor heterostructure comprises a GaAs/AlGaAs heterostructure.

7. A sensor according to claim 1 wherein the semiconductor heterostructure comprises a plurality of alternating layers of two different semiconductor materials.

8. A sensor according to claim 7 wherein said alternating layers comprise GaAs and AlGaAs.

9. A sensor according to claim 1 wherein the semiconductor heterostructure comprises a series of alternating heterointerfaces that allow multiple uses of the heterostructure by progressive etching of the heterostructure material to sequentially expose the heterointerfaces of interest.

10. A sensor according to claim 1 wherein the charged molecule of interest is a biomolecule.

11. A sensor according to claim 10 wherein the biomolecule comprises one of a bacterium and a virus.

12. A sensor according to claim 11 wherein the exterior layer is functionalized using an antibody corresponding to said one of a bacterium and a virus.

13. A sensor according to claim 1 wherein the heterostructure comprises a photoluminescent material that emits a photoluminescence signal in response to the heterostructure being illuminated by the predetermined optical signal, the photoluminescence signal changing in a manner indicative of said rate of photocorrosion, and wherein the means for detecting a rate of photocorrosion comprises a photoluminscence detector.

14. A sensor according to claim 1 wherein the solution under test also functions as the etching fluid.

15. A photo-electrochemical biosensor comprising:
an etching fluid;
a semiconductor heterostructure located in the etching fluid that has an exterior layer that is stable in the absence of a predetermined optical signal and that undergoes photocorrosion by the etching fluid when illuminated by said optical signal, illumination of the heterostructure by said optical signal further causing the emission of photoluminescence that changes with a progression of the photocorrosion;
a self-assembled monolayer (SAM) deposited on said exterior layer, the SAM providing a specific adherence to a biomolecule of interest, such that contact between the SAM and a solution under test results in immobilization by the SAM of a quantity of said biomolecule that corresponds to its concentration in the solution, wherein the immobilized biomolecules alter a rate of said photocorrosion such that a rate of change in said photoluminescence is indicative of said quantity of biomolecules immobilized on the SAM;
an illumination source for providing a controlled illumination of the heterostructure with the predetermined optical signal; and
a photoluminescence detection system for monitoring the photoluminescence.

16. A photo-electrochemical sensor for detecting the concentration of a charged molecule of interest in a solution under test comprising:
an etching fluid;
a semiconductor heterostructure located in the etching fluid that has an exterior layer that is stable in the absence of a predetermined optical signal and that undergoes photocorrosion by the etching fluid when illuminated by said optical signal, the exterior layer being functionalized to provide a specific adherence to the charged molecule of interest, such that contact between the exterior layer and the solution under test results in immobilization of a quantity of said charged molecule on the exterior layer that corresponds to its concentration in the test solution;
an illumination source for providing a controlled illumination of the heterostructure with the predetermined optical signal; and
a detection system that detects a rate of photocorrosion of said exterior layer, said photocorrosion rate being influenced by the immobilized molecules in a manner that is indicative of said quantity of biomolecules immobilized on the exterior layer.

17. A sensor according to claim 16 wherein the exterior layer of the heterostructure is functionalized using a self-assembled monolayer (SAM) deposited on said exterior layer, the SAM providing said specific adherence to the charged molecule of interest.

18. A sensor according to claim 17 wherein the SAM comprises an alkanethiol based material.

19. A sensor according to claim 17 wherein the SAM is treated with a chemical reagent that precipitates sulphur.

20. A sensor according to claim 16, wherein the quantity of said charged molecule of interest that is immobilized corresponds to an amount of electrical charge in proximity to said exterior layer.

21. A sensor according to claim 16 wherein the semiconductor heterostructure comprises a GaAs/AlGaAs heterostructure.

22. A sensor according to claim 16 wherein the semiconductor heterostructure comprises a plurality of alternating layers of two different semiconductor materials.

23. A sensor according to claim 16 wherein the semiconductor heterostructure comprises a series of alternating heterointerfaces that allow multiple uses of the heterostructure by progressive etching of the heterostructure material to sequentially expose the heterointerfaces of interest.

24. A sensor according to claim 16 wherein the charged molecule of interest is a biomolecule.

25. A sensor according to claim 24 wherein the biomolecule comprises one of a bacterium and a virus.

26. A sensor according to claim 25 wherein the exterior layer is functionalized using an antibody corresponding to said one of a bacterium and a virus.

27. A sensor according to claim 16 wherein the solution under test also functions as the etching fluid.

* * * * *